(12) United States Patent
Stout et al.

(10) Patent No.: US 7,557,197 B2
(45) Date of Patent: Jul. 7, 2009

(54) HUMAN SOLUBLE NEUROPILIN-1 PRIMARY POLYADENYLATION SIGNAL AND USES THEREOF

(75) Inventors: J. Timothy Stout, Portland, OR (US); Trevor McFarland, Portland, OR (US); Peter J. Francis, Weybridge (GB); Binoy Appukuttan, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 167 days.

(21) Appl. No.: 11/046,219

(22) Filed: Jan. 28, 2005

(65) Prior Publication Data

US 2005/0175591 A1    Aug. 11, 2005

Related U.S. Application Data

(60) Provisional application No. 60/539,857, filed on Jan. 28, 2004.

(51) Int. Cl.
*C07H 21/02*    (2006.01)
*C12N 15/00*    (2006.01)
*A01N 43/04*    (2006.01)
(52) U.S. Cl. .................... 536/23.1; 435/455; 514/44
(58) Field of Classification Search ............ 536/23.1; 435/455; 514/44
See application file for complete search history.

(56) References Cited

U.S. PATENT DOCUMENTS

| 4,399,216 A | 8/1983 | Axel et al. ............... 435/6 |
| 5,122,458 A | 6/1992 | Post et al. ............... 435/69.1 |
| 6,531,123 B1 * | 3/2003 | Chang ................ 424/93.2 |

OTHER PUBLICATIONS

Rossignol et al. Genomics 70:211-222, 2000.*
Soker et al. J. Cell. Biochem. 85:357-368; 2001.*
Quensel et al. J. Cell Biochem. 85:403-409; 2002.*
Cackowski et al., "Identification of two novel alternatively spliced Neuropilin-1 isoforms," *Genomics*, 84(1):82-94, 2004.
Gagnon et al., "Identification of a natural soluble neuropilin-1 that binds vascular endothelial growth factor: In vivo expression and antitumor activity," *Proc. Natl. Acad. Sci. USA*, 97(6):2573-2578, 2000.

* cited by examiner

*Primary Examiner*—Fereydoun G Sajjadi
(74) *Attorney, Agent, or Firm*—Klarquist Sparkman, LLP

(57) ABSTRACT

The human soluble neuropilin-1 (sNRP) polyadenylation signal (sNRP-poly(A)), situated downstream of the GT splice donor site of intron 12 of the full-length neuropilin-1 gene, also functions as the termination codon for sNRP. This 17 nucleotide sequence efficiently facilitates addition of poly(A) tails to RNAs expressed in cells. The present invention shows that this optimally succinct sequence has similar activity to the SV40 polyadenylation signal that is currently used in expression vectors. By using this shorter dual termination/polyadenylation signal and avoiding the need for large and cumbersome polyadenylation signals, expression vectors may be engineered to carry considerably larger genes.

29 Claims, 6 Drawing Sheets

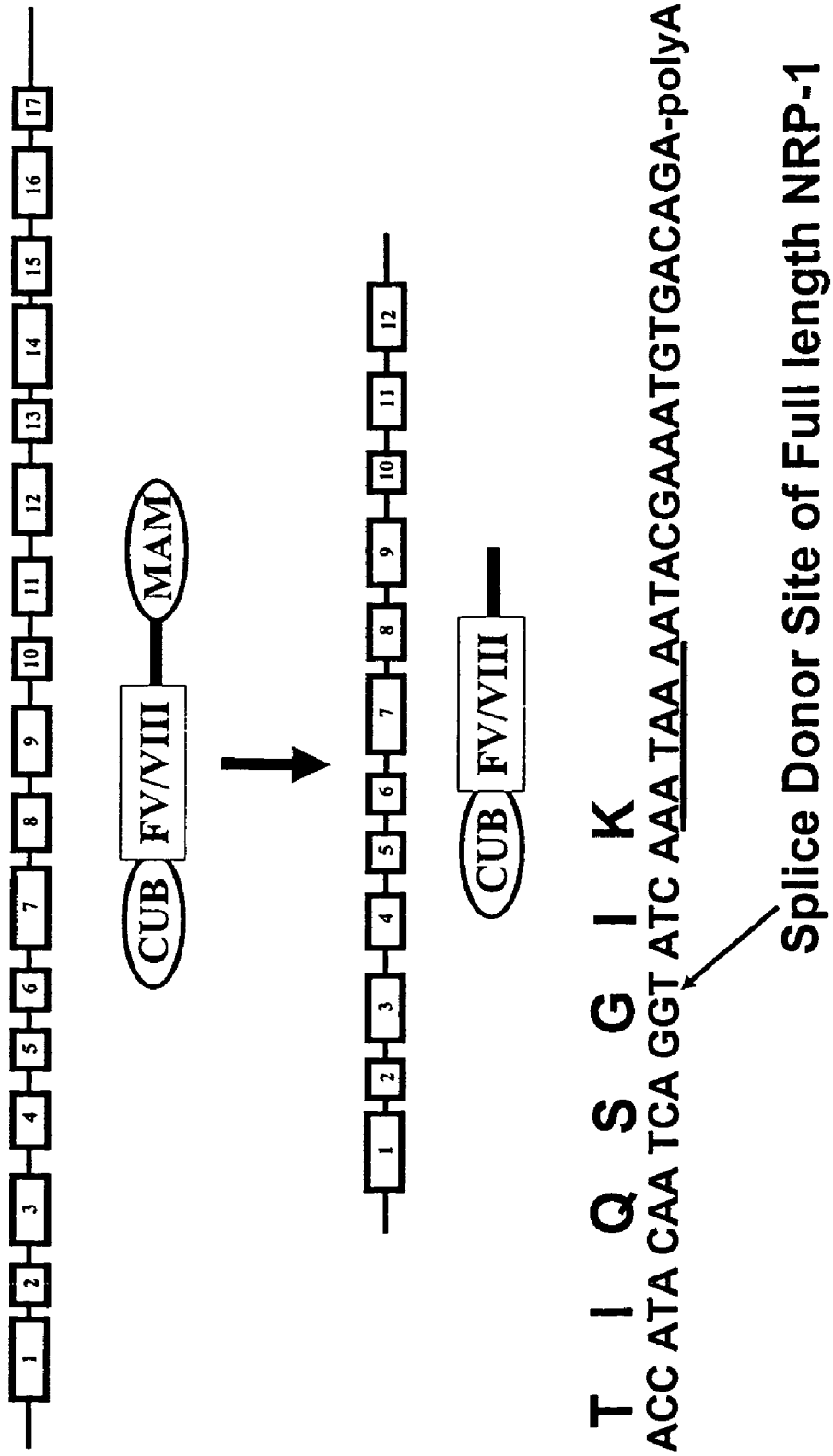

Difference in Polyadenylation Signal Size

Soluble neuropilin-1 polyadenylation signal

<u>AAATAAAAT</u>ACGAAATG

17bp

SV40 polyadenylation signal

GCTAGCTCGACATGATAAG
ATACATTGATGAGTTTGGAC
AAACCACAACTAGAATGCA
GTGAAAAAATGCTTTATTT
GTGAAATTTGTGATGCTATT
GCTTTATTTGTGAAATTTGT
GATGCTATTGCTTTATTTGT
AACCATTATAAGCTGCAATA
AACAAGTTAACAACAACAAT
TGCATTCATTTTATGTTTCAG
GTTCAGGGGGAGGTGTGGG
AGGTTTTTAAAGCAAGTAA
AACCTCTACAAATGTGGTAG
ATCATTTAAATGTTAAT

SEQUENCE LISTING

```
<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
aaataaaata cgaaatg                                                     17

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
ggccacgcgt cgactagtac tttttt                                           26
```

HUMAN SOLUBLE NEUROPILIN-1 PRIMARY POLYADENYLATION SIGNAL AND USES THEREOF

RELATED U.S. APPLICATION DATA

This application claims priority to provisional application No. 60/539,857, filed on Jan. 28, 2004.

FIELD OF THE INVENTION

The present invention relates generally to the field of eukaryotic gene expression. More specifically, the present invention provides a human soluble neuropilin-1 primary polyadenylation signal (which also acts as a termination codon) for efficient mRNA termination/translation, as well as being useful in genetic engineering and construction of viral vectors.

BACKGROUND OF THE INVENTION

Polyadenylation, the process by which a 3' poly-adenosine (poly(A)) tail is added to a eukaryotic pre-mRNA, affords stability to the RNA molecule and is essential for subsequent protein translation. In addition, the process contributes to transcriptional termination, correct cellular mRNA targeting, effective splicing and the regulation of gene expression.

The primary and secondary genomic sequences that initiate polyadenylation have been extensively studied. Primary sequences, typically located within 30 base pairs of the stop codon, are highly conserved and generally conform to: AAUAAA or AUUAAA. Most single base-pair substitutions significantly reduce polyadenylation efficiency with the exception of AUUAAA. Secondary polyadenylation sequences, comprising various combinations of less-well characterized G-U rich pentamers, are found distributed over several hundred base pairs downstream. Their precise role is unclear and their presence not essential for polyadenylation. These secondary sequences, however, may serve to enhance the polyadenylation process by contributing to the architecture of the pre-mRNA molecule.

Neuropilin-1 cell surface glycoprotein that acts as a receptor for semaphorin/collapsin family proteins, mediators of neuronal guidance, as well as for vascular endothelial growth factor. Neuropilin-1 can also be expressed as a soluble form.

The ability of viruses to cross the plasma membrane and harness a cell's transcriptional/translational apparatus has been extensively utilized for the purposes of gene therapy and molecular biological research. One shortcoming of such technologies is that vectors that integrate into the genome and thereby have the potential to achieve long-term stable gene expression are limited in the amount of genetic material they may carry.

Commercially available vectors have a genomic backbone that includes sequences for replication and one or more cloning sites for the insertion of genetic material. Usually, a sequence containing a polyadenylation signal, that may be greater than two hundred base-pairs, is usually included immediately downstream of the multiple cloning site. By shortening the polyadenylation sequence, it seems reasonable that a vector could be engineered to carry a larger gene.

The prior art is deficient in providing a short polyadenylation sequence that would enable engineers of vectors to carry larger genes. The present invention fulfills this long-standing need and desire in the art by disclosing a short polyadenylation sequence with dual function from human soluble neuropilin-1 (sNRP).

SUMMARY OF THE INVENTION

Polyadenylation of mRNA is essential for expression of genes from eukaryotic polymerase II promoters. Poly(A) tails protect RNA from 3'-5' degradation, facilitate transport to the cytoplasm, and greatly enhance translation from the RNA. For these reasons polyadenylation signal sequences are requisite components of eukaryotic polypeptide expression vectors. Conventional polyadenylation sequences can be greater than 200 nucleotides in length. The length of these sequences can be problematic especially in the context of viral expression vectors in which only a limited stretch of nucleotides can be packaged. The present invention addresses this problem by providing the polyadenylation signal of soluble neuropilin-1 (sNRP) (SEQ ID NO:1, AAATAAAATACGAAATG), a functional polyadenylation signal of only 17 nucleotides.

In one embodiment of the present invention there is provided an isolated DNA molecule comprising a sNRP polyadenylation signal defined by SEQ ID NO:1. The words "isolated DNA molecule" in this specification refer to any polymer of deoxyribonucleic acid that is purified such that it is substantially free of genomic DNA. Some non-limiting examples of isolated DNA molecules include synthetic oligonucleotides, polymerase chain reaction (PCR) products, plasmid vectors, viral vectors, cosmids, and yeast artificial chromosomes. When ever the term "polyadenylation signal" is used to herein what is meant is a sequence sufficient to direct the addition of polyadenosine ribonucleic acid to an RNA expressed in a cell.

In a preferred embodiment of the present invention a heterologous polypeptide coding region is positioned upstream of SEQ ID NO:1 in an isolated DNA molecule. One, two, three or more polypeptide coding regions may be positioned upstream or SEQ ID NO:1. Wherein multiple polypeptide coding regions are positioned upstream of SEQ ID NO:1 these coding regions may be operably linked by IRES sequences. As used herein "heterologous polypeptide coding region" refers to any polypeptide coding region that does not encode soluble neuropilin-1 protein.

In a further embodiment of the present invention a promoter region is positioned upstream of a heterologous polypeptide coding region and SEQ ID NO:1. The promoter may comprise a cellular promoter, a viral promoter, a chimeric promoter, an engineered promoter, a tissue specific promoter, an inducible promter, or other types of promoters. Some non-limiting examples of viral promoters are the cytomegalovirus immediate early (CMV) promoter, retroviral LTR promoters (e.g. HTLV), the AAV ITR promoter SV40 promoters and papilloma virus promoters. Some of the cellular promoters that could be used include, but are not limited to, promoters for interleukin-2, beta-interferon, collagenase, actin, and platelet-derived growth factor. In a more preferred embodiment the promoter is the CMV immediate early promoter. Other examples of promoters which could be used are provided throughout the specification.

In a preferred embodiment of the present invention it is contemplated that, SEQ ID NO:1 could be positioned in frame with a heterologous polypeptide coding region. For the purpose of this specification the term "in frame" means that translation of said polypeptide coding region would continue into sequence corresponding to SEQ ID NO:1, such that nucleotides 4 through 6 of SEQ ID NO:1 may constitute a translation stop codon.

In further embodiments of the present invention, SEQ ID NO:1 is positioned such that the 5' six nucleotides of SEQ ID NO:1 replace the last three nucleotides and stop codon of a polypeptide coding region. In this arrangement, SEQ ID NO:1 can function as both a polyadenylation signal and a translation termination signal for a polypeptide coding region.

It is contemplated that a heterologous polypeptide coding region of the invention could comprise a reporter gene. Some examples of reporter genes that might be used are fluorescent proteins, such as humanized red-shifted green fluorescent protein (hrGFP), beta-galactosidase and luciferase. In a yet more preferred embodiment the polypeptide coding region of a invention is hrGFP. Examples of other reporter genes are give throughout the specification.

It is also contemplated that a heterologous polypeptide coding region could comprise a therapeutic gene. Some non-limiting examples of therapeutic genes contemplated are Bik, Bad, Bak, Bax, Bcl-2, Bcl-XL, Gax, X-linked inhibitor of apoptosis protein (XIAP), cellular inhibitor of apoptosis protein (cIAP)-1, cIAP-2, p16, p21, p27, p53, retinoblastoma gene (pRb), the constitutively active form of pRb, PTEN, tissue inhibitor of metalloproteinase (TIMP)-1, TIMP-2, TIMP-3, TIMP-4, endostatin, angiostatin, endostatin XVIII, endostatin XV, the C-terminal hemopexin domain of matrix metalloproteinase-2, the kringle 5 domain of human plasminogen, a fusion protein of endostatin and angiostatin, a fusion protein of endostatin and the kringle 5 domain of human plasminogen, the monokine-induced by interferon-gamma (Mig), the interferon-alpha inducible protein 10 (IP-10), a fusion protein of Mig and IP-10, soluble FLT-1 (fms-like tyrosine kinase 1 receptor), and KDR (kinase insert domain receptor). Examples of other therapeutic genes are given throughout the specification.

In preferred embodiment of the invention the isolated DNA molecule of the invention can be a vector. As used herein a "vector" may be defined as a replicable DNA construct to which another DNA segment may be attached so as to bring about the replication of the attached segment. Vectors maybe used to amplify and/or express DNA encoding a polypeptide. Vectors contemplated herein include, but are not limited to, plasmid vectors and viral vectors.

The present invention also may comprise a viral vector. The short length of SEQ ID NO:1(17 nucleotides), compared to conventional polyadenylation signals that can be hundreds nucleotides in length, enables construction of viral vector encoding larger polypeptides. Some examples of viral vectors contemplated in the present invention include, but are not limited to retrovirus, adenovirus, adeno-associated virus, SV40 and herpes virus vectors. In a preferred embodiment of the present invention the viral vector comprises a lentivirus vector. Some examples include, but are not limited to, human immunodeficiency virus, and simian immunodeficiency virus vectors.

The invention also encompasses a method for expressing a polypeptide in a cell. In this method an isolated DNA molecule which may comprise a promoter, polypeptide coding region and (SEQ ID NO:1) is delivered to a cell. Expression of the DNA molecule in the cell thus mediates expression of said polypeptide in the cell. Delivery of said DNA molecule to a cell may be accomplished by micro-injection, by transfection, or by transduction or by other means that are known in the art.

In preferred embodiments the method of the invention could be used to express a polypeptide in a tissue culture cell, or in a cell that is part of a tissue. In a further embodiment said cell could be an animal, fungus or insect cell. In yet more preferred embodiments the cell could be a human cell. Some examples of cell types contemplated herein that include, but are not limited to a, retinal, corneal, trabecular, lenicular, retinal pigment epithial, proliferative vitreoretinopathic, and vascular endothelial cell.

In a preferred method for expressing a polypeptide in cells. A viral vector comprising a promoter, a polypeptide coding region and SEQ ID NO:1 can be transduced into a cell. This method constitutes packaging said viral vector into a recombinant virus produced by a method which is well known in the art. Said recombinant virus is placed in contact with a cell thus mediating expression of the viral vector in the cell. For the purpose of this specification the term "transduce" and its derivations "transducing", "transduced" and "transduction" refer to a method of expressing a nucleic acid in a cell by contacting the cell with a recombinant virus wherein the said nucleic acid is the payload of said virus. Some non-limiting examples of viral vectors that may be used in this method include retrovirus, adenovirus, adeno-associated virus, SV40 and herpes virus vectors. In a preferred embodiment of this method the viral vector may be a lentivirus.

The use of the word "a" or "an" when used in conjunction with the term "comprising" in the claims and/or the specification may mean "one," but it is also consistent with the meaning of "one or more," "at least one," and "one or more than one." As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1 Shows the genomic structure of human soluble neuropilin-1. The dual termination/polyadenylation signal is within intron 12 of full length neuropilin-1 (SEQ ID NO:3 and (SEQ ID NO:4).

FIG. 2 Shows the soluble neuropilin-1 and SV40 polyadenylation signals (SEQ ID NO:1 and (SEQ ID NO:5).

DETAILED DESCRIPTION OF THE INVENTION

The ability to reliably transfect and transduce cells in vitro or in vivo has become a mainstay of molecular biological research. One of the shortcomings of the current generation of viral vectors engineered to be stably integrative and therefore provide long term gene expression in their host cells is that the amount of genetic material they may carry is limited to at most 2-3 kb. A polyadenylation signal, such as SV40, frequently of around 250 base pairs is usually included immediately downstream of any multiple cloning site to drive efficient polyadenylation of RNA. By shortening this sequence, it seems reasonable that a vector could be engineered to carry a larger gene.

The human soluble neuropilin-1 alternative polyadenylation site (sNRP-poly(A), situated between the $5^{th}$ through $10^{th}$ bp downstream of the GT splice donor site of intron 12 of the full length neuropilin-1 gene, comprises only the primary poly (A) sequence, -AATAAA-. Intriguingly, this signal begins at the second base pair of the last codon AAA that codes for amino acid lysine (Kolodkin, et al., 1997). The -TAA- sequence (situated between 7-9 bp downstream of the GT splice donor site of intron 12 of the full length neuropilin-1 gene, see FIG. 1) of the poly (A) is used as a termination signal. Thus, this particular poly (A) sequence has dual function.

The present invention demonstrates that this primary signal is not only sufficient for the addition of a poly(A) tail to a pre-mRNA molecule, but also sufficient, when positioned in the appropriate reading frame, to mediate translation termination of a polypeptide coding region. Data presented below show that when SEQ ID NO:1 was positioned downstream of a gene such as the human recombinant green fluorescent protein (hrGFP) and delivered to target cells, efficient expression of hrGFP was observed. Furthermore, RT-PCR and DNA sequencing confirmed that polyadenylation must be occurring as a result of this primary sequence and not due to the presence of another poly(A) signal.

Figure 6:
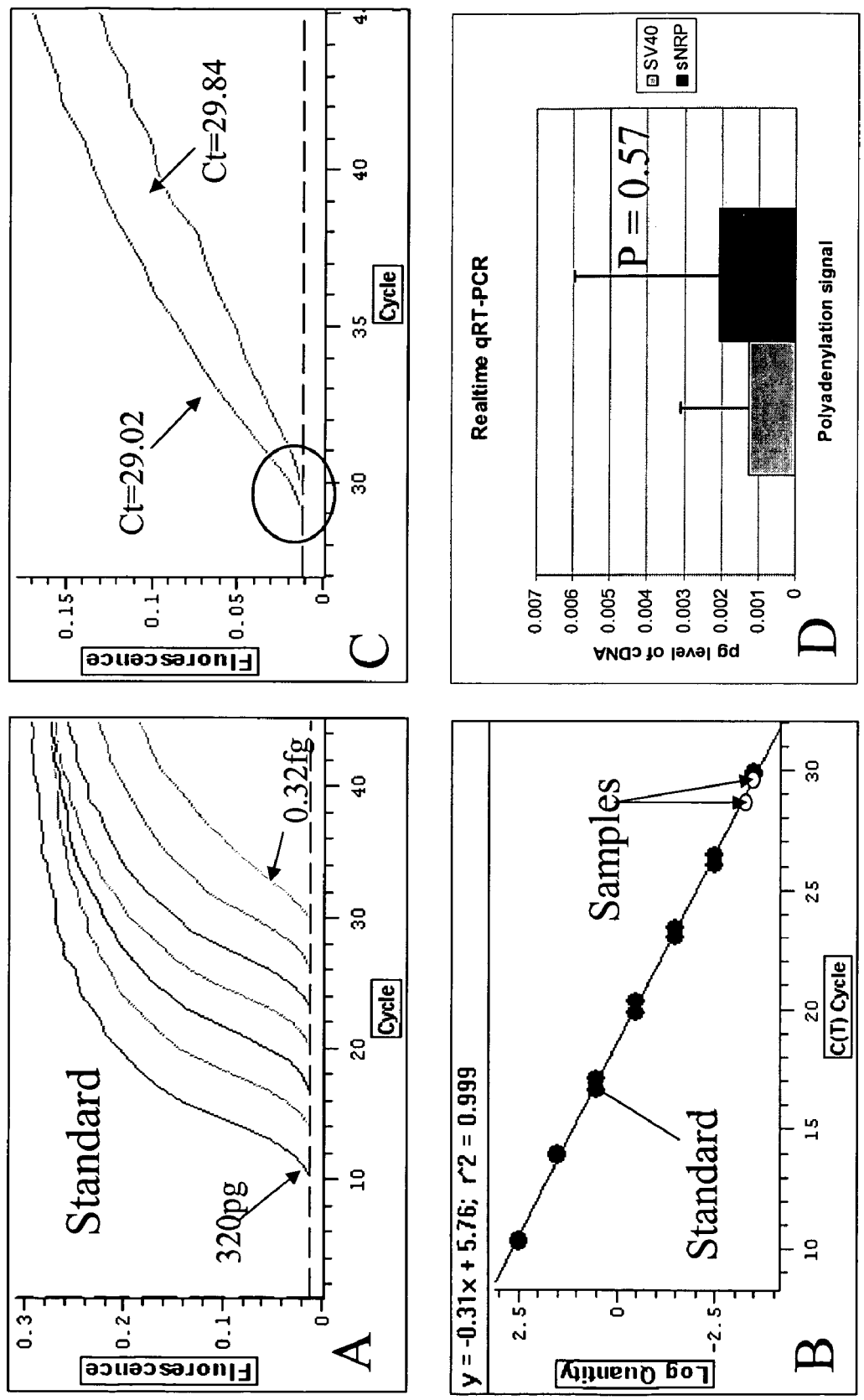
FIG. 6 Demonstrates that RNA polyadenylated by the sNRP polyadenylation signal is expressed with similar efficiency as RNA that is polyadenylated via the SV40 polyadenylation signal. (A) Serial dilutions of plasmid standards show even cycling distribution by, real time PCR, indicating 10 fold dilutions were consistent and valid. (B) Standard curve results were linear and samples fell within standard curve albeit on the lower range. OPTICON software was used to calculate pg levels of product. (C) Raw data demonstrating Cycle Threshold (Ct), results indicate Ct values were nearly equivalent. (D) Graphical representation of the data showing pg levels of the two products were insignificantly different.

In some cases, the polyadenylation proceeds independent of any known downstream elements (Takagaki and Manley, 1997), though less efficiently (Zarudnaya et al., 2003), probably due to the ability of the polyadenylation apparatus to make use of the many different structural conformations of downstream RNA sequences. However the efficiency of polyadenylation mediated by SEQ ID NO:1 was also found to be similar to that of the much larger SV40 polyadenylation signal sequence (FIG. 6). This data showed that though most genes encode, secondary downstream polyadenylation enhancer sequences these elements are not required for efficient function of the sNRP polyadenylation signal (SEQ ID NO:1). Thus, the present invention indicates that the soluble neuropilin-1 dual termination/polyadenylation signal can be conveniently incorporated into gene expression vectors to enable the vectors to carry larger genes for therapeutic benefit due to the use of a shorter polyadenylation signal.

Nucleic Acids

The present invention concerns nucleic acids. A "nucleic acid" as used herein will generally refers to a molecule of DNA or RNA comprising a sequence of nucleotide bases. A nucleotide base includes purine or pyrimidine bases found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 3 and about 100 nucleotide bases in length. The term "polynucleotide" refers to at least one molecule of greater than about 100 nucleotide bases in length.

a. Preparation of DNA

DNA encoding SEQ ID NO:1 may be made by any technique known to one of ordinary skill in the art, such as for example, chemical synthesis, enzymatic production or biological production. Non-limiting examples of a synthetic DNA (e.g., a synthetic oligonucleotide), include DNA made, in vitro, by chemically synthesis using phosphotriester, phosphite or phosphoramidite chemistry and solid phase techniques such as described in EP 266,032 or via deoxynucleoside H-phosphonate intermediates as described by Froehler et al., 1986 and U.S. Pat. No. 5,705,629. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244.

A non-limiting example of an enzymatically produced DNA include one produced by enzymes in amplification reactions such as PCR™ (see for example, U.S. Pat. Nos. 4,683, 202 and 4,682,195).

A non-limiting example of a biologically produced nucleic acid includes a recombinant nucleic acid produced (i.e., replicated) in a living cell, such as a recombinant DNA vector replicated in bacteria (see for example, Sambrook et al. 2001).

The isolated DNA molecule encoding the sNRP polyadenylation signal (SEQ ID NO:1) may comprise a contiguous nucleic acid sequence consisting of the sequence of SEQ ID NO:1 and additional nucleotides or base pairs. Such sequences may be identical or complementary to SEQ ID NO:1.

b. Purification of Nucleic Acids

A nucleic acid may be purified on polyacrylamide gels, cesium chloride centrifugation gradients, or by any other means known to one of ordinary skill in the art (see for example, Sambrook et al., 2001). In preferred aspects, a nucleic acid is a pharmacologically acceptable nucleic acid. Pharmacologically acceptable compositions are known to those of skill in the art, and are described herein.

The present invention concerns a nucleic acid that is an isolated DNA molecule. As used herein, the term "isolated DNA molecule" refers to a nucleic acid molecule (e.g. DNA) that has been isolated free of, or is otherwise free from, the bulk of the total genomic and transcribed nucleic acids of one or more cells. In certain embodiments, "isolated DNA molecule" refers to a nucleic acid that has been isolated free of, or is otherwise free of, bulk of cellular components or in vitro reaction components such as for example, macromolecules such as lipids or proteins, small biological molecules, and the like.

Polypeptide Coding Regions

Polypeptide coding region also encompasses the "protein coding region". The term "polypeptide coding region" refers to any DNA sequence which comprises at least three adjacent codons, wherein a codon is a three nucleotide sequence that can be interpreted as an amino acid by cellular translation apparatus. Codons may code for specific amino acids, that well known in the art, or may signal the termination of translation (in the case of codons corresponding to TAA, TAG, or TGA triplets). Since codons consist of nucleotide triplets a nucleic acid can be interpreted by the translation apparatus in three possible phases. The phase that codes for a polypeptide, and lacks intervening termination codons, is called the "open reading frame" of said polypeptide coding region.

A polypeptide coding region of the invention, may, in some embodiments consist of a reporter gene. What is meant by a "reporter gene" is a sequence that when expressed a cell can be detected by a method which is known to those skilled in the art. Methods for detection of reporter genes include, but are not limited to, immuno-blot, enzyme linked immuno-absorbent assay (EISA), detection of fluorescence or luminescence via microscopy or use of luminometers/flourometers, or reporter genes may be virtue of their expression in a cell confer resistance to certain cytotoxic compounds. Some non-limiting examples of reporter genes contemplated herein include humanized red shifted green fluorescent protein (hrGFP), enhanced green fluorescent protein (eGFP), CAT, Neomycin resistance marker (NEO), Hygromycin resistance marker, Puromycin resistance marker, beta-galactosidase, and luciferase.

In preferred embodiments of the invention a polypeptide coding region may comprise a therapeutic gene. The term "therapeutic gene" used throughout this application refers to any gene that when administered to a subject promotes or enhances the well-being of the subject with respect to the medical treatment of his/her condition. Examples conditions that may be treated include, but are not limited to, pre-cancer, cancer, and hyperproliferative diseases. Preferred examples of conditions which could be treated include ocular diseases exemplified by, age-related macular degeneration, proliferative diabetic retinopathy, retinopathy of prematurity, glaucoma, and proliferative vitreopathy. Other examples of conditions that may be treated are give through-out the specification.

Some non-limiting examples of therapeutic genes contemplated for use the invention are Bik, Bad, Bak, Bax, Bcl-2, Bcl-XL, Gax, X-linked inhibitor of apoptosis protein (XIAP), cellular inhibitor of apoptosis protein (cIAP)-1, cIAP-2, p16, p21, p27, p53, retinoblastoma gene (pRb), the constitutively active form of pRb, PTEN, tissue inhibitor of metalloproteinase (TIMP)-1, TIMP-2, TIMP-3, TIMP-4, endostatin, angiostatin, endostatin XVIII, endostatin XV, the C-terminal hemopexin domain of matrix metalloproteinase-2, the kringle 5 domain of human plasminogen, a fusion protein of endostatin and angiostatin, a fusion protein of endostatin and the kringle 5 domain of human plasminogen, the monokine-induced by interferon-gamma (Mig), the interferon-alpha inducible protein 10 (IP-10), a fusion protein of Mig and IP-10, soluble FLT-1 (fms-like tyrosine kinase 1 receptor), and KDR (kinase insert domain receptor). Examples of other therapeutic genes are given throughout the specification.

Variation of a Polypeptide Coding Region

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within 2 is preferred, those that are within +1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

Vectors for Cloning, Gene Transfer, and Expression

Within certain embodiments expression vectors are employed to express the polypeptide product. In some embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products also are provided, as is an element that links expression of the drug selection markers to expression of the polypeptide.

a. Promoter sequences

In preferred embodiments, the isolated DNA molecule encoding a polypeptide is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter employed to control the expression of a nucleic acid sequence of interest is not believed to be important, so long as it is capable of direction the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the human T-cell leukemia virus LTR promoter (HTLV), the SV40 early promoter, the Rous sarcoma virus long terminal repeat, rat insulin promoter and glyceraldehyde-3-phosphate dehydrogenase can be used to obtain high-level expression of the polypeptide coding region of the invention. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transduction can be optimized. Further, selection of a promoter that is regulated in response to specific physiologic signals can permit inducible expression of the gene product. Promoters that permit expression of a protein of interest generally under most conditions and in most cell types is termed constitutive, and an example of this is the CMV promoter. A tissue-specific promoter is a regulatable promoter that is allows expression only in particular tissues or cells. Tables 2 and 3 list several elements/promoters that may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression vector (Table 2 and Table 3). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression vector.

Tables 1 and 2, below, list a variety of regulatory signals for use according to the present invention.

TABLE 1

Inducible Elements

| Element | Inducer | References |
| --- | --- | --- |
| MT II | Phorbol Ester (TPA) Heavy metals | Palmiter et al., 1982; Haslinger and Karin, 1985; Searle et al., 1985; Stuart et al., 1985; Imagawa et al., 1987; Karin et al., 1987; Angel et al., 1987b; McNeall et al., 1989 |

TABLE 1-continued

Inducible Elements

| Element | Inducer | References |
|---|---|---|
| MMTV (mouse mammary tumor virus) | Glucocorticoids | Huang et al., 1981; Lee et al., 1981; Majors and Varmus, 1983; Lee et al., 1984; Ponta et al., 1985 |
| β-Interferon | poly(rI)X poly(rc) | Tavernier et al., 1983 |
| Adenovirus 5 E2 | Ela | Imperiale and Nevins, 1984 |
| Collagenase | Phorbol Ester (TPA) | Angel et al., 1987a |
| Stromelysin | Phorbol Ester (TPA) | Angel et al., 1987b |
| SV40 | Phorbol Ester (TFA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | Ela, SV40 Large T Antigen | Taylor et al., 1989; Taylor and Kingston, 1990a, b |
| Proliferin | Phorbol Ester-TPA | Mordacq and Linzer, 1989 |
| Tumor Necrosis Factor | MA | Hensel et al., 1989 |
| Thyroid Stimulating Hormone α Gene | Thyroid Hormone | Chatterjee et al., 1989 |

TABLE 2

Other Promoter/Enhancer Elements

| Promoter/Enhancer | References |
|---|---|
| Immunoglobulin Heavy Chain | Banerji et al., 1983; Gillies et al., 1983; Grosschedl and Baltimore, 1985; Atchison and Perry, 1986, 1987; Imler et al., 1987; Neuberger et al., 1988; Kiledjian et al., 1988; |
| Immunoglobulin Light Chain | Queen and Baltimore, 1983; Picard and Schaffner, 1985 |
| T-Cell Receptor | Luria et al., 1987, Winoto and Baltimore, 1989; Redondo et al., 1990 |
| HLA DQ α and DQ β | Sullivan and Peterlin, 1987 |
| β-Interferon | Goodbourn et al., 1986; Fujita et al., 1987; Goodbourn and Maniatis, 1985 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRα | Sherman et al., 1989 |
| β-Actin | Kawamoto et al., 1988; Ng et al., 1989 |
| Muscle Creatine Kinase | Jaynes et al., 1988; Horlick and Benfield, 1989; Johnson et al., 1989a |
| Prealbumin (Transthyretin) | Costa et al., 1988 |
| Elastase I | Ornitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987, Tronche et al., 1989, 1990 |
| α-Fetoprotein | Godbout et al., 1988; Campere and Tilghman, 1989 |
| γ-Globin | Bodine and Ley, 1987; Perez-Stable and Constantini, 1990 |
| β-Globin | Trudel and Constantini, 1987 |
| c-fos | Cohen et al., 1987 |
| c-HA-ras | Triesman, 1985; Deschamps et al., 1985 |
| Insulin | Edlund et al., 1985 |
| Neural Cell Adhesion Molecule (NCAM) | Hirsch et al., 1990 |
| $a_1$-Antitrypain | Latimer et al., 1990 |
| H2B (TH2B) Histone | Hwang et al., 1990 |
| Mouse or Type I Collagen | Rippe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |

TABLE 2-continued

Other Promoter/Enhancer Elements

| Promoter/Enhancer | References |
|---|---|
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987 Schaffner et al., 1988 |
| Polyoma | Swartzendruber and Lehman, 1975; Vasseur et al., 1980; Katinka et al., 1980, 1981; Tyndell et al., 1981; Dandolo et al., 1983; Hen et al., 1986; Campbell and Villarreal, 1988 |
| Retroviruses (e.g. HTLV) | Kriegler and Botchan, 1983; Kriegler et al., 1984a, b; Bosze et al., 1986; Miksicek et al., 1986; Celander and Haseltine, 1987; Thiesen et al., 1988; Celander et al., 1988; Chol et al., 1996; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987, Stephens and Hentschel, 1987 |
| Hepatitis B Virus | Bulla and Siddiqui, 1988; Jameel and Siddiqui, 1986; Shaul and Ben-Levy, 1987; Spandau and Lee, 1988 |
| Human Immunodeficiency Virus | Muesing et al., 1987; Hauber and Cullan, 1988; Jakobovits et al., 1988; Feng and Holland, 1988; Takebe et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 |

In any event, it will be understood that promoters are DNA elements which when positioned functionally upstream of a gene leads to the expression of that gene. Most transgene constructs of the present invention are functionally positioned downstream of a promoter element.

b. Encoding Multiple Polypeptide Coding Regions in the Same RNA

Internal ribosome entry sites (IRESs) are used to create multigene, or polycistronic, messages. IRES elements are able to bypass the ribosome scanning mode of 5' 7-methylguanosine (cap)-dependent translation and begin translation at internal sites (Pelletier and Sonenberg, 1988). IRES elements can be linked to heterologous polypeptide coding regions. Thus multiple open reading frames, encoding polypeptides, can be transcribed together, each separated by an IRES, creating polycistronic messages. By virtue of the IRES, each open reading frame is accessible to ribosomes for efficient translation. Therefore multiple genes can be efficiently expressed using a single promoter/enhancer to transcribe a single message. Some exemplar viral and cellular IRES sequences are listed in table 4, however this list does not recite all possible IRES sequences that may be employed.

TABLE 3

Exemplary IRES sequences

| Viral internal ribosome entry sites | Cellular internal ribosome entry sites |
|---|---|
| Poliovirus (PV) (Roberts et al 1998) | c-myc (Nanbru et al., 1997) |
| Hepatitis C virus (HCV) (Otto et al 2004) | XIAP (U.S. Pat. No. 6,171,821) |
| Hepatitis A virus (HAV) (Roberts et al 1998) | BCL-2 (Shirrell et al. 2004) |
| Cricket paralysis virus (Wilson et al 2000) | c-IAP-1 (Van Eden et al. 2004) |
| Human immunodeficiency virus (HIV) (Buck et al. 2001) | DAP-5 (Henis-Korenblit et al. 2000) |

TABLE 3-continued

Exemplary IRES sequences

| Viral internal ribosome entry sites | Cellular internal ribosome entry sites |
|---|---|
| Foot and Mouth disease virus (FMDV) (Roberts et al 1998) | eIF4G (Johannes et al. 1998) |
| Encephalomyocarditis virus (EMCV) (Roberts et al 1998) | BiP (Macejak et al. 1991) |
| Human rhinovirus (HRV) (Roberts et al 1998) | |

In preferred embodiments for the present invention multiple polypeptide coding regions, separated by IRES sequences, may be positioned upstream of SEQ ID NO:1. For example a polypeptide coding region may comprise a therapeutic gene, wherein another polypeptide coding region comprises a reporter gene. In this configuration the expression of the therapeutic gene may be easily monitored by virtue of the reporter gene that is co-expressed from the same transcript.

Non-Viral Nucleic Acid Delivery to a Cell

DNA molecules of the invention may be delivered to cells via methods which are known to those skilled in the art. In some embodiments, DNA molecules or vectors of the invention can be delivered to cells by methods that do not require viral vectors. In a preferred embodiment DNA molecules or vectors of the invention can be delivered to cells to allow for in vivo change of genotype and/or modulation of phenotype of cells in a plurality of tissues of a mammalian host. For instance DNA molecules of the invention could be delivered into a circulating body fluid at a sufficient dose to cause transfection of tissues and cells contacted by the nucleic acid. The tissues which are could be transformed include the lungs, heart, liver, bone marrow, spleen, lymph nodes, kidneys, thymus, skeletal muscle, ovary, uterus, stomach, small intestine, colon, pancreas, and brain in normal animals, as well as metastatic tumors and intravascular tumor emboli in tumor-bearing mammals. Another example of delivery of nucleic acids or vectors of the invention could be topical for instance in an eye drop. Method detailed below indicate ways in which DNA or vector of the invention might be delivered to cells or tissues either in vitro or in vivo. Some non-limiting examples of non-viral DNA delivery techniques include:

a. Chemical Transfection

In some embodiments of the invention DNA molecules may be delivered to cells by calcium phosphate precipitation. This method is well known to those skilled in the art (Maniatis, Fritsch & Sambrook, "Molecular Cloning: A Laboratory Manual", 1982).

b. Liposomal Delivery

In a further embodiment of the invention, the gene construct may be entrapped in a liposome or lipid formulation. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a gene construct complexed with Lipofectamine (Gibco BRL). In a preferred embodiment a DNA or vector of the invention could be delivery by a cationic liposome, such as by the method disclosed in U.S. Pat. No. 6,806,084.

Recent advances in lipid formulations have improved the efficiency of gene transfer in vivo (Smyth-Templeton et al., 2003; WO 98/07408). A novel lipid formulation composed of an equimolar ratio of 1,2-bis(oleoyloxy)-3-(trimethyl ammonio)propane (DOTAP) and cholesterol significantly enhances systemic in vivo gene transfer, approximately 150-fold. The DOTAP:cholesterol lipid formulation is said to form a unique structure termed a "sandwich liposome". This formulation is reported to "sandwich" DNA between an invaginated bi-layer or 'vase' structure. Beneficial characteristics of these lipid structures include a positive colloidal stabilization by cholesterol, two dimensional DNA packing and increased serum stability.

c. Electroporation

The application of brief, high-voltage electric pulses to a variety of animal cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by means of electroporation, is well-known to those of skill in the art. In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding. To effect transformation by electroporation one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol dependent on the nature of the newly incorporated DNA.

d. Microprojectile Bombardment

A further advantageous method for delivering transforming DNA segments to cells is microprojectile bombardment. In this method, particles may be coated with nucleic acids and delivered into cells by a propelling force. Exemplary particles include those comprised of tungsten, gold, platinum, and the like.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 h post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

e. Protamine

Protamine may also be used to form a complex with an expression construct. Such complexes may then be formulated with the lipid compositions described above for administration to a cell. Protamines are small highly basic nucleoproteins associated with DNA. Their use in the delivery of nucleic acids is described in U.S. Pat. No. 5,187,260, which is incorporated by reference. U.S. patent application Ser. No. 10/391,068 (filed Mar. 24, 2003), which pertains to methods and compositions for increasing transduction efficiency of a viral vector by complexing the viral vector with a protamine molecule, is specifically incorporated by reference herein.

Virus Mediated Nucleic Acid Delivery or Transduction

There are a number of ways in which expression vectors may be introduced into cells. In certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986). In other case Vectors derived from viruses such as vaccinia virus (Ridgeway, 1988; Baichwal and Sugden, 1986; Coupar et al., 1988) have been employed. However the extensive cytopathic effect caused by these vectors have limited their use to short term expression of polypeptides in laboratory experiments. Some non-limiting examples of viruses contemplated herein for nucleic acid delivery are detailed below.

a. Herpes Viral Infection

In some embodiments, the vector is Herpes simplex virus (HSV). A factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

b. Adenoviral Infection

One method for delivery of the recombinant DNA involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a recombinant gene construct that has been cloned therein.

The adenovirus vector may be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the some starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus growth and manipulation is known to those of skill in the art, and exhibits broad host range in vitro and in vivo. This group of viruses can be obtained in high titers, e.g., $10^9$-$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

c. Retroviral Infection

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants.

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, when simple retroviruses are used, integration and stable expression require the division of host cells (Paskind et al., 1975). I In preferred embodiments of the invention, complex retroviruses, or lentiviruses are contemplated for use as vectors delivery to cells. Unlike simple retroviruses, lentiviruses have the ability to transduce non-dividing cells, even cells traditionally refractor to gene transfer such as human retinal, corneal, trabecular, lenicular, retinal pigment epithial, proliferative vitreoretinopathic, and vascular endothelial cells. Additionally lentiviral vectors may be preferred in some embodiments of the present invention since under natural conditions of infection lentivirus is an intraocular pathogen that does not induce inflammatory responses. Previous work has demonstrated the successful use of lentivirus in the transduction of both neuronal and retinal cells (Naldini et al. 1996; Miyoshi et al. 1997).

d. Adeno-associated Viral Infection

Adeno-associated virus (AAV) is an attractive vector system for use in the present invention as it has a high frequency of integration and it can infect nondividing cells, thus making it useful for delivery of genes into mammalian cells in tissue culture (Muzyczka, 1992). AAV has a broad host range for infectivity (Tratschin et al., 1984; Laughlin et al., 1986; Lebkowski et al., 1988; McLaughlin et al., 1988), which means it is applicable for use with the present invention. Details concerning the generation and use of rAAV vectors are described in U.S. Pat. Nos. 5,139,941 and 4,797,368, each incorporated herein by reference.

Studies demonstrating the use of AAV in gene delivery include Zhou et al. (1993); Flotte et al. (1993); and Walsh et al. (1994). Recombinant AAV vectors have been used successfully for in vitro and in vivo transduction of marker genes (Kaplitt et al., 1994; Lebkowski et al., 1988; Samulski et al., 1989; Shelling and Smith, 1994; Yoder et al., 1994; Zhou et al., 1994; Hermonat and Muzyczka, 1984; Tratschin et al., 1985; McLaughlin et al., 1988) and genes involved in human diseases (Flotte et al., 1992; Ohi et al., 1990; Walsh et al., 1994; Wei et al., 1994). Recently, an AAV vector has been approved for phase I human trials for the treatment of cystic fibrosis.

Typically, recombinant AAV (rAAV) virus is made by co-transfecting a plasmid containing the gene of interest flanked by the two AAV terminal repeats (McLaughlin et al., 1988; Samulski et al., 1989; each incorporated herein by reference) and an expression plasmid containing the wild-type AAV coding sequences without the terminal repeats, for example pIM45 (McCarty et al., 1991; incorporated herein by reference). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994; Clark et al., 1995). Cell lines carrying the rAAV DNA as an integrated provirus can also be used (Flotte et al., 1995).

Pharmaceutical Compositions

Pharmaceutical compositions of the present invention are also contemplated. The phrases "pharmaceutical or pharmacologically acceptable" refers to molecular entities and compositions that do not produce an adverse, allergic or other untoward reaction when administered to an animal, such as, for example, a human. The preparation of a pharmaceutical composition including isolated DNA and vectors described herein will be known to those of skill in the art in light of the present disclosure, as exemplified by Remington's Pharmaceutical Sciences, 18th Ed. Mack Printing Company, 1990. Moreover, for animal (e.g., human) administration, it will be understood that preparations should meet sterility, pyrogenicity, general safety and purity standards as required by FDA Office of Biological Standards.

"Therapeutically effective amounts" are those amounts effective to produce beneficial results in the recipient animal or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990). Except insofar as any conventional carrier is incompatible with the active ingredient, its use in the therapeutic or pharmaceutical compositions is contemplated.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Alternatively, a patient may be given $1 \times 10^{-5}$, $10^{-6}$, $10^{-6}$, $10^{-7}$, $10^{-8}$, $10^{-9}$, $10^{-10}$, $10^{-11}$, $10^{-12}$ M of a substance (or any range derivable therein), such as a nucleic acid or vector of the invention, in a volume of 0.1 µl, 1.0 µl, 10 µl, 100 µl, 1 ml, 5 ml, 10 ml, 20 ml, 25 ml, 50 ml, 100 ml, 200 ml, 300 ml, 400 ml, 500 ml, or more (or any range derivable therein). Inhibitors may be administered 1, 2, 3, 4, 5, 6, 7, 8, 9, 10 or more times over a course of 1, 2, 3, 4, 5, 6, 7, 8, 9 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, 1, 2, 3, 4, 5, 6, 7, 8, 9, 10, 11, 12 months, or 1, 2, 3, 4, 5, 6, 7, 8, 9, 10 or more years on a regular or as needed basis.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The compositions of the present invention may comprise different types of carriers depending on whether it is to be administered in solid, liquid or aerosol form, and whether it need to be sterile for such routes of administration as injection.

The compositions may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments, the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments, the compositions are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition should be stable under the conditions of manufacture and storage, and preserved against the contaminating action of microorganisms, such as bacteria and fungi. It will be appreciated that exotoxin contamination should be kept minimally at a safe level, for example, less that 0.5 ng/mg protein.

Routes of Administration

DNA molecules or vectors of the present invention may be administered intravenously, intradermally, intraarterially, intraperitoneally, intralesionally, intracranially, intraarticularly, intraprostaticaly, intrapleurally, intratracheally, intranasally, intravitreally, intravaginally, intrauterinely, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (Remington's, 1990).

In a preferred embodiment, DNA or vectors of the invention may be delivered to the eye into the capsular, vitreal or sub-retinal space.

Combination Therapies

In order to increase the effectiveness of a treatment with the compositions of the present invention, such are expression vector or viral vectors, it may be desirable to combine these compositions with other therapies effective in the treatment of specific diseases or conditions.

The compositions of the present invention can precede or follow the other agent treatment by intervals ranging from minutes to weeks. It is contemplated that one may administer both modalities within about 12-24 h of each other and, more preferably, within about 6-12 h of each other. In some situations, it may be desirable to extend the time period for treatment significantly, where several days (2, 3, 4, 5, 6 or 7) to several weeks (1, 2, 3, 4, 5, 6, 7 or 8) lapse between the respective administrations.

Various combinations may be employed where a composition including a nucleic acid of the invention inhibitor is "A" and the secondary agent, is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | |
| B/A/B/A | B/A/A/B | A/A/A/B | B/A/A/A | A/B/A/A | A/A/B/A | | a. EXAMPLE 1

RT-PCR, mRNA Isolation and Sequencing

Cells were homogenized and RNA isolated using the RNAqueous kit (Ambion Inc., Austin, Tex.). RT-PCR was then performed using an oligo d(T) reverse primer which at the 3' end had the following "linker" sequence: 5'-GGC-CACGCGTCGACTAGTACTTTTTT-3' (SEQ ID NO:2). hrGFP-mRNA amplification was then performed, using the forward primer and reverse primer designed to anneal to the "linker" sequence to enable the identification of the exact point of polyadenylation. Sequencing was undertaken using the di-deoxy chain termination reaction and an ABI PRISM 310®.

b. EXAMPLE 2

Plasmid Preparation

Human recombinant green fluorescent protein (hrGFP) was amplified by PCR to either contain the dual function sNRP-poly (A)/termination signal, -AATAAA- (the termination codon is underlined) or a disrupted polyadenylation signal (-AATGAA-) that contains an alternative termination codon. The PCR fragments were ligated into the pAAV or pUC18 vectors. The green fluorescent protein was under the transcriptional control of the cytomegalovirus (CMV) promoter. The constructions were confirmed by direct sequencing of the transgene insert.

Direct sequencing confirmed the successful mutagenesis of the penultimate codon of hrGFP from GTG to AAA and the insertion of the human soluble neuropilin-1 (sNRP) stop codon TAA followed by the remainder of the sNRP polyadenylation signal. The change in the codon prior to the termination codon replaces the amino acid valine for lysine in the native protein. A control construct was engineered in which the termination codon, TAA, was substituted with the alternative termination codon, TGA, thereby maintaining functionality of protein termination but eliminating the polyadenylation signal.

c. EXAMPLE 3

Transfecting Experiments

Human 293T microvascular endothelial cells were grown to 50% confluence in Dulbecco's Modified Eagle Medium (D-MEM, 5% FBS, 1% P&S) at 37° C., normoxia. The cells were transfected by the calcium phosphate co-precipitation method and cultured in D-MEM at 37° C., normoxia, for 24 hours. Thereafter the media was replaced with D-MEM containing 10 mM Na butyrate and 20 mM Hepes buffer (pH 7.02). Translation of hrGFP protein was thein visualized using a Leica DMIRB fluorescence microscope.

Figure 3:
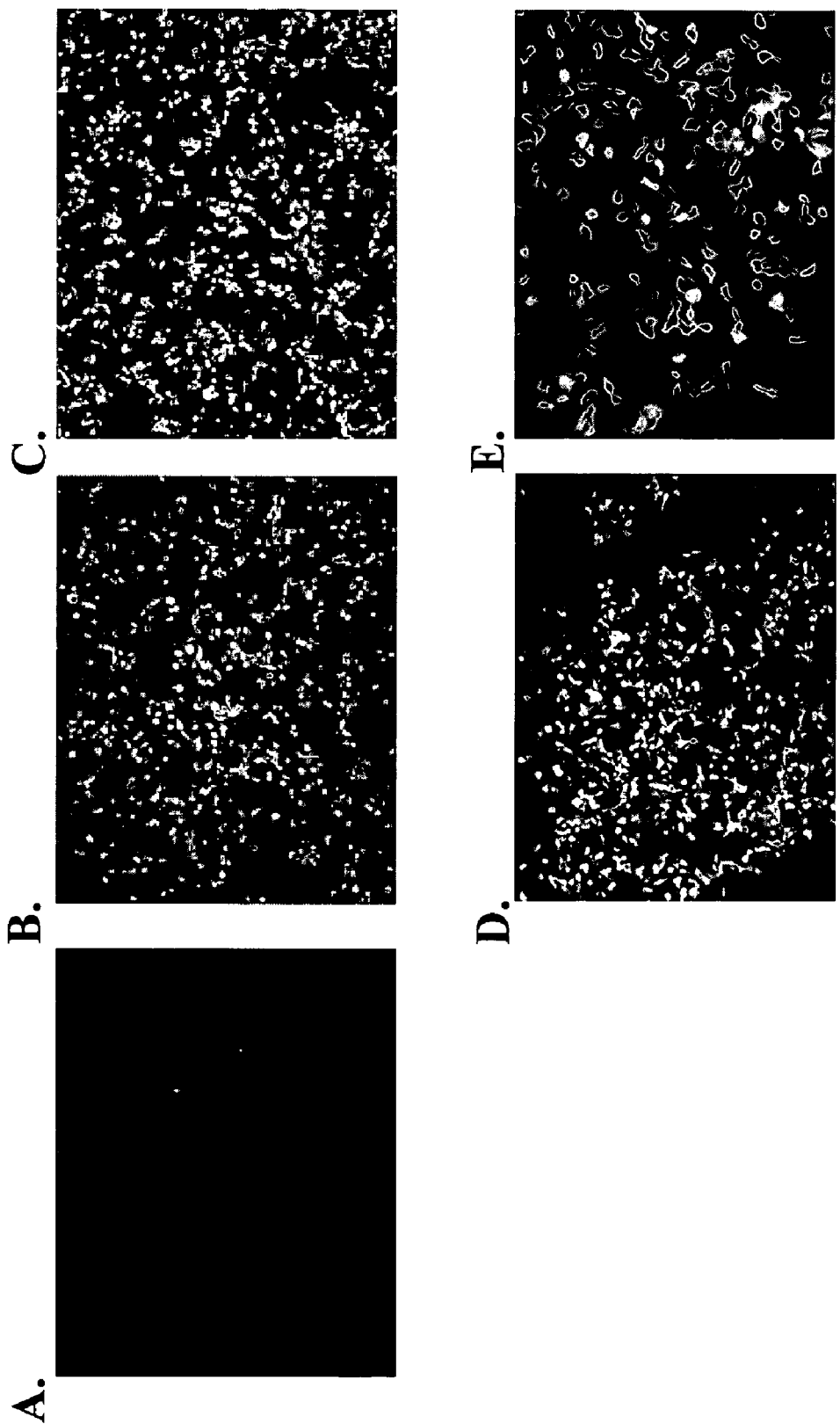
FIG. 3 Fluorescence microscopy of 293T cells 24 hours after transfection with pUC18-cmv-hrGFP-no poly(A) (A) pUC18-cmv-hrGFP-sNRP poly(A) (B) pUC18-cmv-hrGFP-SV40 poly(A) (C) pAAV-cmv-hrGFP-sNRP poly(A) (D); or pAAV-cmv-hr-GFP-SV40 poly(A) (E)

293T cells were transfected with adeno-associated viral plasmids (pAAV) or the expression vector pUC18 containing appropriate inserts (Table 5). pAAV containing human recombinant green fluorescent protein (hrGFP) whose transcription was driven by the CMV promoter with polyadenylation directed by the SV40 poly (A) signal was used as a positive control (pAAV-cmv-hrGFP-SV40). pUC18 carrying hrGFP with no polyadenylation signal were used as a negative control (pUC18-cmv-hrGFP-NO poly(A)). FIG. 3 shows the results of those experiments at the 24 hour time-point. Efficient and abundant expression was seen in cells transfected with the recombinant hrGFP-sNRP-poly(A). No expression was seen in cells transfected with hrGFP-NO poly(A).

Figure 4:
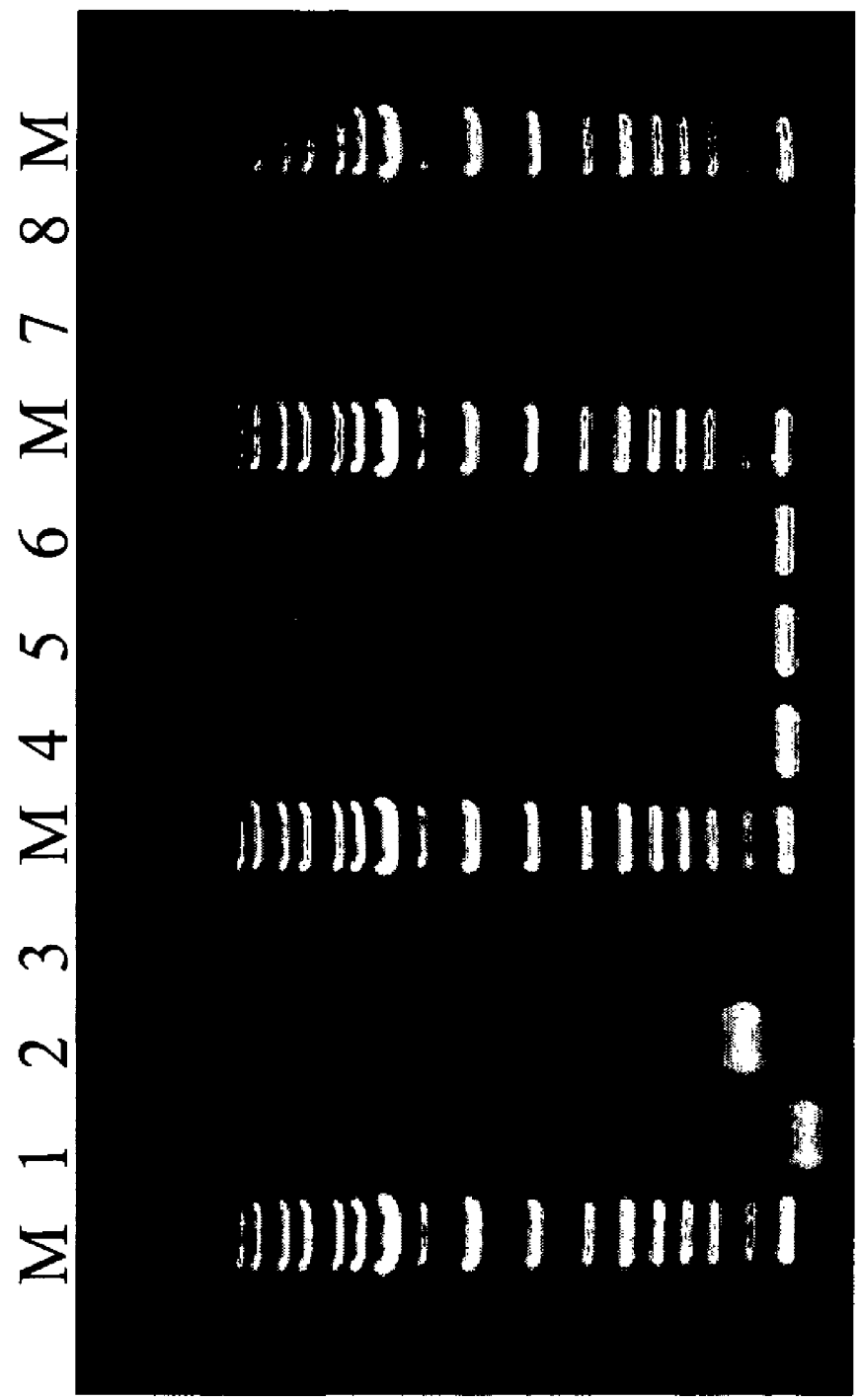
FIG. 4 RT-PCR products resolved in agarose gel and visualized with ethidium bromide staining. Lanes 1 to 3 used an oligo dT reverse primer and a forward primer matching sequence in the 3' end of hrGFP. Sample RNA was extracted from cells trasfected with pUC18-cmv-hrGFP-sNRP poly(A) (lane 1), pUC18-cmv-hrGFP-SV40 poly(A) (lane 2) or pUC18-cmv-hrGFP-no poly(A) (lane 3). Lanes 4 to 6 are positive control RT-PCR products which amplified portions of endogenous beta-actin from the same RNA samples analyzed in lanes 1 to 3 respectively. Lanes 7 and 8 negative control RT-PCR reactions (RT enzyme was excluded) for RNA extracted from pUC18-cmv-hrGFP-sNRP poly(A), or pUC18-cmv-hrGFP-SV40 poly(A) transfected cells respectively. M indicates a DNA ladder.

RT-PCR was performed on those cells expressing hrGFP using gene-specific primers that would amplify the poly(A) tail to reveal the precise polyadenylation start position. FIG. 4 shows that hrGFP mRNA from 293T cells transfected with pUC18-hrGFP-sNRP poly(A) was shorter in length compared to message[s] from cells transfected with pUC18-hrGFP-WV40 poly(A), indicating different polyadenylation start sites. No containment bands were seen, suggesting that no other polyadenylation sites were being utilized by the transcription apparatus.

Figure 5:
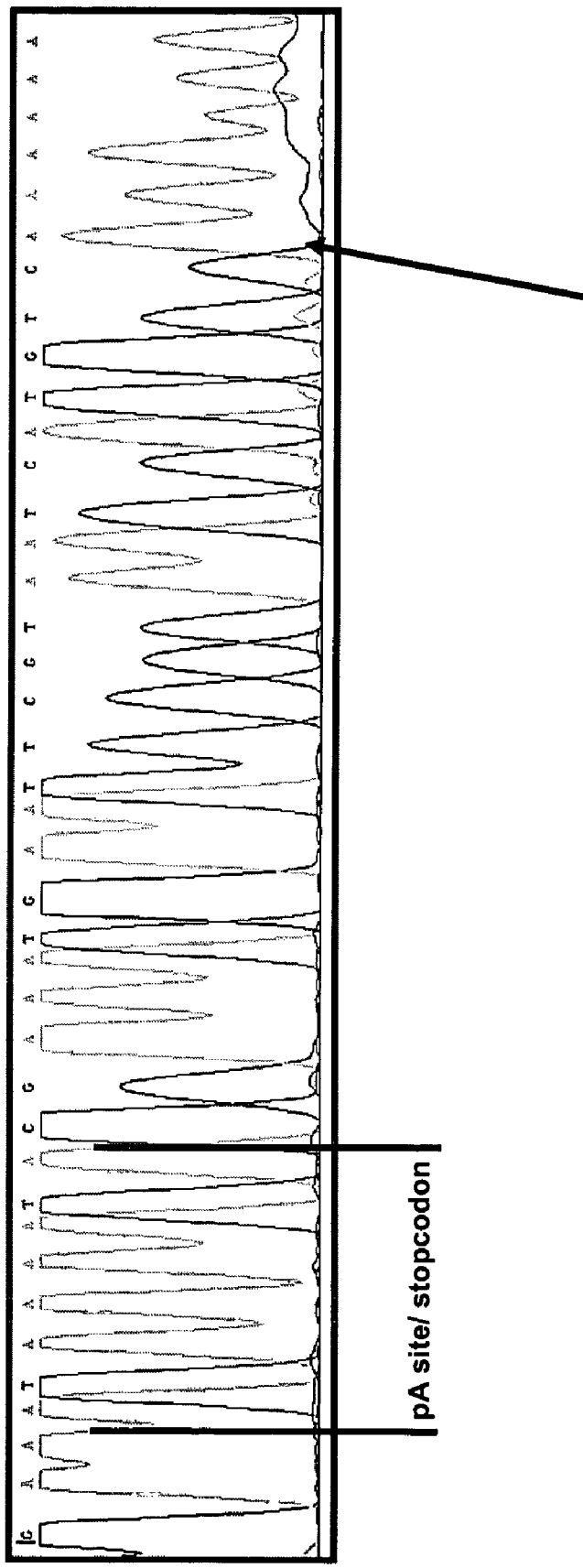
FIG. 5 Shows an electrophoretogram sequence of hrGFP mRNA with soluble neuropilin-1 polyA region. This sequence demonstrates efficient termination and polyadenylation of the mRNA.

Direct sequencing showed that polyadenylation in pAAV/pUC18-cmv-hrGFP-sNRP poly(A) commenced at a predictable position 9 nucleotides downstream of the stop codon (FIG. 5), whereas in pAAV/pUC18-cmv-hrGFP-SV40 poly (A) polyadenylation started 100 base pairs downstream of the stop codon (data not shown).

To determine the efficiency of polyadenylation samples were obtained from 293T cells transfected with CaPO4 using 15 ug of either pUC18-CMV-hrGFP-SV40 or pUC18-CMV-hrGFP-sNRpA. RNA was isolated and then quantified using the Ribogreen method. RNA from each sample (150 ng) was reverse transcribed using an OligodT primer. PCR was performed with the HS-Taq SYBR Green PCR kit (MJR) and run on a Chromo4 thermocycler (MJR) to quantify any difference in transcript copy number. Serially diluted purified plasmid was used for the standard, dilutions ranged from 320 pg to 0.32 fg. All samples and standards were run in triplicate. The results from this experiment demonstrate that copy number was not altered with the use of the truncated sNRP1 polyadenylation signal (pA). This suggests that the sNRP1 pA signal is as efficient as the SV40 pA in this particular experiment.

TABLE 4

Plasmid Constructs

| Plasmid | Promoter | Gene | Polyadenylation Signal | Experimental role | hrGFP detected | Polyadenylation start position |
|---|---|---|---|---|---|---|
| pAAV | CMV | hrGFP | Human sNRP1 | Test | Yes | 9 |
| pUC18 | CMV | hrGFP | SV40 | Positive control | Yes | 156 |
| pUC18 | CMV | hrGFP | Human sNRP1 | Test | Yes | 9 |
| PUC18 | CMV | hrGFP | None | Negative control | No | N/A | hrGFP was detected by fluorescence microscopy and RT-PCR.
The polyadenylation start position is relative to the hrGFP stop codon.

REFERENCES

The following references were cited herein:
U.S. Pat. No. 6,806,084
U.S. Pat. No. 6,171,821
U.S. Pat. No. 5,705,629
U.S. Pat. No. 5,602,244
U.S. Pat. No. 5,574,146
U.S. Pat. No. 5,554,744
U.S. Pat. No. 5,428,148
U.S. Pat. No. 5,264,566
U.S. Pat. No. 5,187,260
U.S. Pat. No. 5,141,813
U.S. Pat. No. 5,139,941
U.S. Pat. No. 4,959,463
U.S. Pat. No. 4,816,571
U.S. Pat. No. 4,797,368
U.S. Pat. No. 4,682,195
U.S. Pat. No. 4,683,202
U.S. Pat. No. 4,659,774
U.S. Pat. No. 4,554,101
U.S. patent application Ser. No. 10/391,068
E.P. Patent 266,032
WO 98/07408
Angel et al., *Cell* 49(6):729-39, 1987.
Angel et al., *Mol Cell Biol* 7(6):2256-66, 1987.
Baichwal and Sugden, "Vectors for gene transfer derived from animal DNA viruses: Transient and stable expression of transferred genes", In: *Gene Transfer*, Kucherlapati R, ed., New York, Plenum Press, pp. 117-148, 1986.
Banerji et al., *Cell* 27(2):299-308, 1981.
Banerji et al., *Cell* 33(3):729-40, 1983.
Berkhout et al., *J. Virol.*, 63(12):5501-5504, 1989.
Blanar et al., *Embo. J.*, 8(4):1139-1144, 1989.
Boshart et al., *Cell*, 41(2):521-530, 1985.
Bosze et al., *EMBO. J.*, 5(7):1615-1623, 1986.
Braddock et al., *Cell*, 58(2):269-279, 1989.
Bodine et al., *Embo. J.*, 6(10):2997-3004, 1987.
Buck, et al., *J. Virol.*, 75:181-191, 2001.
Bulla et al., *J. Virol.*, 62(4):1437-1441, 1988.
Campbell et al., *Mol. Cell Biol.*, 8(5):1993-2004, 1988.
Campbell, In: *Monoclonal Antibody Technology, Laboratory Techniques in Biochemistry and Molecular Biology*, Burden and Von Knippenberg (Eds.), Elseview, Amsterdam, 13:71-74/75-83, 1984.
Campo et al., *Nature*, 303(5912):77-80, 1983.
Celander et al., *J. Virol.*, 61(2):269-75, 1987.
Celander et al., *J. Virol.*, 62(4):1314-22, 1988.
Chang et al., *Mol. Cell Biol.*, 9(5):2153-62, 1989.
Chatterjee et al., *Proc. Natl. Acad. Sci. USA*, 86(23):9114-8, 1989.
Chol et al., *Err J Biochem* 239(3):579-87, 1996.
Clark et al., *Hum. Gene Ther.*, 6(10):1329-41, 1995.
Coffin, In: *Virology*, Fields et al., eds., Raven Press, New York, pp. 1437-1500, 1990
Cohen et al., *J. Cell Physiol. Suppl.*, 5:75-81, 1987.
Costa et al., *Mol. Cell Biol.*, 8(1):81-90, 1988.
Couch et al., *Am. Rev. Resp. Dis.*, 88:394-403, 1963.
Coupar et al., *Gene*, 68:1-10, 1988.
Cripe et al., *EMBO. J.*, 6(12):3745-53, 1987.
Culotta et al., *Mol. Cell. Biol.*, 9(3):1376-1380, 1989.
Dandolo et al., *J. Virol.*, 47(1):55-64, 1983.
Deschamps et al., *Science*, 230(4730):1174-1177, 1985.
Edbrooke et al., *Mol. Cell Biol.*, 9(5):1908-1916, 1989.
Edlund et al., *Science*, 230(4728):912-916, 1985.
Feng et al., *Nature*, 334(6178):165-167, 1988.
Firak et al., *Mol. Cell Biol.*, 6(11):3667-3676.
Foecking et al., *Gene*, 45(1):101-105, 1986.
Flotte et al., *Am. J. Respir. Cell Mol. Biol.*, 7(3):349-356, 1992.
Flotte et al., *Proc. Natl. Acad. Sci. USA*, 90(22):10613-10617, 1993.
Flotte, et al., *Gene Ther.*, 2(1):29-37, 1995.
Froehler et al., Nucleic Acids Res., 14:5399-5407.
Ghosh and Bachhawat, Targeting of Liposomes to Hepatocytes. In: *Liver Diseases, Targeted Diagnosis and Therapy Using Specific Receptors and Ligands*. Wu et al., eds., Marcel Dekker, New York, pp. 87-104, 1991.
Gloss et al., *Embo. J.*, 6(12):3735-3743, 1987.
Godbout et al., *Mol. Cell. Biol.*, 8:1169, 1988.
Goodbourn and Maniatis, *Cell*, 41(2):509-520, 1985.
Goodbourn et al., *Cell*, 45(4):601-610, 1986.
Greene et al., *Adv. Exp. Med. Biol.*, 254:55-60, 1989.
Haslinger et al., *Proc. Natl. Acad. Sci. USA*, 82(24):8572-8576, 1985.
Hauber et al., *J. Virol.*, 62(3):673-679, 1988.
Hen et al., *Nature*, 321(6067):249-251, 1986.
Hensel et al., *Lymphokine Res.*, 8(3):347-351, 1989.
Henis-Korenblit et al., Mol. Cell. Biol. 20:496-506, 2000.
Hermonat et al., *Proc. Natl. Acad. Sci. USA*, 81(20):6466-6470, 1984.
Herr et al., *Cell*, 45(3):461-470, 1986.
Hirsch et al., *Mol. Cell. Biol.*, 10(5):1959-1968, 1990.
Hirochika et al., *J. Virol.*, 61(8):2599-2606, 1987.
Holbrook et al., *Virology*, 159(1):178-182, 1987.
Horlick et al., *Mol. Cell. Biol.*, 9(6):2396-2413, 1989.

Huang et al., *Cell*, 27(2 Pt 1):245-255, 1981.
Hug et al., *Mol. Cell Biol.*, 8(8):3065-3079, 1988.
Hwang et al., *Mol. Cell Biol.*, 10(2):585-592, 1990.
Imagawa et al., *Cell*, 51(2):251-260, 1987.
Imbra, et al., *Nature*, 323(6088):555-558, 1986.
Imperiale et al., *Mol. Cell Biol.*, 4(5):875-882, 1984.
Jakobovits et al., *Mol. Cell Biol.*, 8(6):2555-2561, 1988.
Jameel et al., *Mol. Cell Biol.*, 6(2):710-715, 1986.
Jaynes et al., *Mol. Cell Biol.*, 8(1):62-70, 1988.
Johannes and Sarnow, *RNA*, 4:1500-1513, 1998.
Johnson et al., *Mol. Cell Biol.*, 9(8):3393-3399, 1989.
Kadesch et al., *Mol. Cell Biol.*, 6(7):2593-2601, 1986.
Karin et al., *Mol. Cell Biol.*, 7(2):606-613, 1987.
Karlsson et al., *EMBO J.*, 5:2377-2385, 1986.
Kaplitt et al., *Nat. Genet.*, 8(2):148-154, 1994.
Katinka et al., *Cell*, 20(2):393-399, 1980.
Klamut et al., *Mol. Cell Biol.*, 10(1):193-205, 1990.
Koch, et al., *Mol. Cell Biol.*, 9(1):303-311, 1989.
Kolodkin et al., *Cell* 90:753-762,1997.
Kawamoto et al., *Mol. Cell Biol.*, 8(1):267-272, 1988.
Kriegler et al., *Blood*, 63(6):1348-1352, 1984.
Kriegler et al., *Cell*, 38(2):483-491, 1984.
Kriegler et al., *Mol. Cell Biol.*, 3(3):325-339, 1983.
Kuhl et al., *Cell*, 50(7):1057-1069, 1987.
Kunz et al., *Nucleic Acids Res.*, 17(3):1121-1138, 1989.
Kyte and Doolittle, *J. Mol. Biol.*, 157:105-132, 1982.
Larsen et al., *J. Biol. Chem.*, 261(31):14373-14376, 1986.
Latimer et al., *Mol. Cell Biol.*, 10(2):760-769, 1990.
Laspia et al., *Cell*, 59(2):283-292, 1989.
Laughlin et al., *J. Virol.*, 60(2):515-524. 1986.
Lebkowski et al., *Mol. Cell Biol.*, 8(10):3988-3996, 1988.
Lee et al., *Nature*, 294(5838):228-232, 1981.
Lee et al., *Nucleic Acids Res.*, 12(10):4191-4206, 1984.
Lin et al., *Mol. Cell Biol.*, 10(2):850-853, 1990.
Luria et al., *EMBO. J.*, 6(11):3307-3312, 1987.
Lusky et al., *Mol. Cell Biol.*, 3(6):1108-1122, 1983.
Lusky et al., Proc. Natl. Acad. Sci. USA, 83(11):3609-3613, 1986.
Macejak and Sarnow, *Nature*, 353:90-94, 1991.
Majors et al., *Proc. Natl. Acad. Sci. USA*, 80(19):5866-5870, 1983.
Mann et al., *Cell*, 33:153-159, 1983.
McCarty et al., *J. Virol.*, 65(6):2936-2945, 1991.
McLaughlin et al., *J. Virol.*, 62(6):1963-1973, 1988.
McNeall et al., *Gene*, 76(1):81-88, 1989.
Miksicek et al., *Cell*, 46(2):283-290, 1986.
Miyoshi et al., *J. Hepatol.* 26:593-605, 1997.
Moreau et al., *Nucleic Acids Res.*, 9(22):6047-6068, 1981.
Mordacq et al., *Genes Dev.*, 3(6):760-769, 1989.
Muesing et al., *Cell*, 48(4):691-701, 1987.
Muzyczka, *Curr. Top Microbiol. Immunol.*, 158:97-129, 1992.
Naldini et al., *Science* 272:263-267, 1996.
Nanbru, et al., *J. Biol. Chem.*, 272:32061-32066, 1997.
Nicolas and Rubenstein, In: *Vectors: A survey of molecular cloning vectors and their users*, Rodriguez and Denhardt (eds.), Stoneham:Butterworth, pp. 493-513, 1988.
Ohi et al., *Gene*, 89(2):279-282, 1990.
Ondek et al., *EMBO. J.*, 6(4):1017-1025, 1987.
Omitz et al., *Mol. Cell Biol.*, 7(10):3466-3472, 1987.
Otto et al., *Cell*, 119:369-380, 2004.
Palmiter et al., *Cell*, 29(2):701-710, 1982.
Paskind et al., *Virology*, 67:242-248, 1975.
Pech et al., *Mol. Cell Biol.*, 9(2):396-405, 1989.
Pelletier and Sonenberg, *Nature*, 334:320-325, 1988.
Perez-Stable et al., *Mol. Cell Biol.*, 10(3):1116-1125, 1990.
Picard et al., *EMBO. J.*, 4(11):2831-2838, 1985.
Pinkert et al., *Genes Dev.*, 1(3):268-276, 1987.
Ponta et al., *Proc. Natl. Acad. Sci. USA*, 82(4):1020-1024, 1985.
Reisman et al., *Oncogene*, 4(8):945-953, 1989.
Remington's Pharmaceutical Sciences, 18th Ed. Mack Printing Company, pp. 1289-1329, 1990.
Ridgeway, "Mammalian expression vectors," In: *Vectors: A Survey of Molecular Cloning Vectors and Their Uses.*, Rodriguez R. L., Denhardt D. T., eds., Butterworth, Stoneham, England, pp. 467-492, 1988.
Rippe et al., *Mol. Cell Biol.*, 9(5):2224-2227, 1989.
Queen and Baltimore, *Cell*, 35:741, 1983.
Quinn et al., *Mol. Cell Biol.*, 9(11):4713-4721, 1989.
Redondo et al., *Science*, 247(4947):1225-1229, 1990.
Resendez et al., *Mol. Cell Biol.*, 8(10):4579-4584, 1988.
Rittling et al., *Nucleic Acids Res.*, 17(4):1619-1633, 1989.
Roberts, et al., *RNA*, 4:520-529, 1998.
Sambrook et al., In: *Molecular cloning*, Cold Spring Harbor Laboratory Press, Cold Spring Harbor, N.Y., 2001.
Samulski et al., *J. Virol.*, 63(9):3822-38228, 1989.
Schaffner et al., *J. Mol. Biol.*, 201(1):81-90, 1988.
Searle et al., *Mol. Cell Biol.*, 5(6):1480-1489, 1985.
Sharp et al., *Cell*, 59(2):229-230, 1989.
Shelling et al., *Gene Ther.*, 1(3):165-169, 1994.
Sherman et al., *Proc. Natl. Acad. Sci. USA*, 86(17):6739-6743, 1989.
Sleigh and Lockett, *EMBO. J.*, 4:3831, 1985.
Shaul et al., *EMBO. J.*, 6(7):1913-1920, 1987.
Sherrill, et al., *J. Biol. Chem.*, 279:29066-29074, 2004.
Smyth-Templeton et al., *Curr. Med. Chem.*, 10:1279-1287, 2003.
Spalholz et al., *Cell*, 42:183, 1985.
Spandidos et al., *EMBO. J.*, 2(7):1193-1199, 1983.
Spandau et al., *J. Virol.*, 62(2):427-434, 1988.
Stephens et al., *Biochem. J.*, 248(1):1-11, 1987.
Stuart et al., *Nature*, 317(6040):828-831, 1985.
Sullivan et al., *Mol. Cell Biol.*, 7(9):3315-3319, 1987.
Swartzendruber et al., *J. Cell Physiol.*, 85(2 Pt 1):179-187, 1975.
Takebe et al., *Mol. Cell Biol.*, 8(1):466-472, 1988.
Takagaki and Manley, *Mol. Biol.* 17:3907-3914, 1997.
Tavernier et al., *Nature*, 301(5901):634-636, 1983.
Taylor et al., *Mol. Cell Biol*, 10(1):176-183, 1990.
Taylor et al., *Science*. 1999 Jul. 2; 285(5424):107-10, 1999.
Temin, "Retrovirus vectors for gene transfer: Efficient integration into and expression of exogenous DNA in vertebrate cell genome," In: *Gene Transfer*, Kucherlapati, ed., Plenum Press, New York, pp. 149-188, 1986.
Thiesen et al., *J. Virol.*, 62(2):614-618, 1988.
Top et al., *J. Infect. Dis.*, 124:155-160, 1971.
Tratschin et al., *Mol. Cell Biol.*, 4(10):2072-2081, 1984.
Tratschin et al., *Mol. Cell Biol.*, 5(11):3251-3260, 1985.
Treisman et al., *Cell*, 42(3):889-902, 1985.
Tronche et al., *Mol. Biol. Med.*, 7(2):173-185, 1990.
Tronche et al., *Mol. Cell Biol.*, 9(11):4759-4766, 1989.
Trudel et al., *Genes Dev.*, 1(9):954-961, 1987.
Tyndall et al., *Nucleic Acids Res.*, 9(23):6231-6250, 1981.
Van Eden, et al., *RNA*, 10:469-481, 2004.
Vasseur et al., *Proc. Natl. Acad. Sci. USA*, 77(2):1068-1072, 1980.
Walsh et al., *J. Clin. Invest.*, 94(4):1440-1448, 1994.
Wang et al., *Cell*, 47(2):241-7, 1986.
Weber et al., *Cell*, 36(4):983-992, 1984.
Wei et al., *Gene Ther.*, 1(4):261-268, 1994.
Wilson, et al., *Mol Cell Biol*, 20:4990-9, 2000.
Winoto et al., *EMBO. J.* 8(3):729-733, 1989.
Yang et al., *J. Virol.*, 68(8):4847-4856, 1994.

Yoder et al., *Blood*, 82(Suppl.):347A, 1994.
Yutzey et al., *Mol. Cell Biol.*, 9(4):1397-1405, 1989.
Zarudnaya, et al., *Nucleic Acids Res.*, 31:1375-1386, 2003.
Zhou et al., *Exp. Hematol.*, 21(7):928-933, 1993.
Zhou et al., *j. Exp. Med.*, 179(6):1867-1875, 1994.

The invention claimed is:

1. An isolated DNA molecule comprising a soluble neuropilin-1 polyadenylation signal as defined by SEQ ID NO:1, further comprising a heterologous polypeptide coding region positioned upstream of the polyadenylation signal.

2. The DNA molecule of claim 1 wherein multiple polypeptide coding regions are separated by IRES sequences.

3. The DNA molecule of claim 1, wherein a promoter is positioned upstream of the heterologous polypeptide and polyadenylation signal.

4. The DNA molecule of claim 3, wherein the promoter is a constitutive promoter.

5. The DNA molecule of claim 3, wherein the promoter is an inducible promoter.

6. The DNA molecule of claim 3, wherein the promoter is a tissue specific promoter.

7. The DNA molecule of claim 4 wherein the stop codon of SEQ ID NO:1 is positioned in-frame with a polypeptide coding region.

8. The DNA molecule of claim 7 wherein SEQ ID NO:1 is positioned such that the 5' six nucleotides of SEQ ID NO:1 replace the last three nucleotides and stop codon of a peptide coding region.

9. The DNA molecule of claim 3, wherein a heterologous coding region comprises a reporter gene.

10. The DNA molecule of claim 9, wherein the reporter gene is selected from the group consisting of humanized red shifted green fluorescent protein (hrGFP), beta-galactosidase, and luciferase.

11. The DNA molecule of claim 3, a wherein the heterologous coding region encodes a gene.

12. The DNA molecule of claim 11, wherein the gene selected from the group consisting of Bik, Bad, Bak, Bax, Bcl-2, Bcl-XL, Gax, X-linked inhibitor of apoptosis protein (XIAP), cellular inhibitor of apoptosis protein (cIAP)-1, cIAP-2, p16, p21, p27, p53, retinoblastoma gene (pRb), the constitutively active form of pRb, PTEN, tissue inhibitor of metalloproteinase (TIMP)-1, TIMP-2, TIMP-3, TIMP-4, endostatin, angiostatin, endostatin XVIII, endostatin XV, the C-terminal hemopexin domain of matrix metalloproteinase-2, the kringle 5 domain of human plasminogen, a fusion protein of endostatin and angiostatin, a fusion protein of endostatin and the kringle 5 domain of human plasminogen, the monokine-induced by interferon-gamma (Mig), the interferon-alpha inducible protein 10 (IP-10), a fusion protein of Mig and IP-10, soluble FLT-1 (fins-like tyrosine kinase 1 receptor), and KDR (kinase insert domain receptor).

13. The DNA molecule of claim 3, wherein said DNA molecule comprises a vector.

14. The DNA molecule of claim 13, wherein the vector is a plasmid vector or a viral vector.

15. The DNA molecule of claim 14, wherein the viral vector is selected from the group consisting of retrovirus, adenovirus, adeno-associated virus, SV40 and herpes virus vectors.

16. The DNA molecule of claim 15, wherein the viral vector is a lentivirus vector.

17. The DNA molecule of claim 13, wherein said DNA molecule comprises a non-viral delivery composition.

18. A method of expressing a polypeptide a cell, comprising the steps of:
  a) delivering the DNA molecule of claim 3 to a eukaryotic cell; and
  b) permitting, expression of the polypeptide.

19. The method of claim 18, wherein the cell is part of a tissue.

20. The method of claim 18, wherein the cell is in an animal.

21. The method of claim 20, wherein the animal is a human.

22. The method of claim 18, wherein the cell is a tissue culture cell.

23. The method of claim 18, wherein the cell is a retinal, corneal, trabecular, lenicular, retinal pigment epithial, proliferative vitreoretinopathic, or vascular endothelial cell.

24. The method of claim 18 wherein the DNA molecule is a plasmid vector or a viral vector.

25. The method of claim 24 wherein the viral vector is selected from the group consisting of retrovirus, adenovirus, adeno-associated virus, SV40 and herpes virus vectors.

26. The method of claim 25 wherein the viral vector is a lentivirus vector.

27. The method of claim 18 wherein the DNA molecule is delivered by transducing the cell with a viral vector.

28. The method of claim 27 wherein the viral vector is selected from the group consisting of retrovirus, adenovirus, adeno-associated virus, SV40 and herpes virus vectors.

29. The method of claim 28 wherein the viral vector is a lentivirus vector.

* * * * *